(12) United States Patent
Yoshikawa et al.

(10) Patent No.: US 8,647,843 B2
(45) Date of Patent: Feb. 11, 2014

(54) METHOD OF PRODUCING SUCCINIC ACID

(75) Inventors: Katsunori Yoshikawa, Suita (JP);
Daisuke Kido, Yokohama (JP); Makoto Murase, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 13/607,049

(22) Filed: Sep. 7, 2012

(65) Prior Publication Data
US 2012/0329095 A1  Dec. 27, 2012

Related U.S. Application Data

(63) Continuation of application No. PCT/JP2011/055355, filed on Mar. 8, 2011.

(30) Foreign Application Priority Data

Mar. 9, 2010 (JP) ................................. 2010-051816

(51) Int. Cl.
*C12P 7/46* (2006.01)

(52) U.S. Cl.
USPC .......................... 435/71.2; 435/132; 435/145

(58) Field of Classification Search
USPC ........................................ 435/71.2, 132, 145
See application file for complete search history.

(56) References Cited

U.S. PATENT DOCUMENTS

| | | | |
|---|---|---|---|
| 4,877,731 A | 10/1989 | Ling et al. | |
| 7,763,447 B2 | 7/2010 | Murase et al. | |
| 2006/0073577 A1 | 4/2006 | Ka-Yiu et al. | |
| 2011/0229945 A1 | 9/2011 | Jansen et al. | |

FOREIGN PATENT DOCUMENTS

| | | |
|---|---|---|
| EP | 2192189 A1 * | 6/2010 |
| JP | 03-505396 | 11/1991 |
| JP | 2003-235592 | 8/2003 |
| JP | 2004-194570 | 7/2004 |
| JP | 2005-095169 | 4/2005 |
| JP | 2006-006344 | 1/2006 |
| JP | 2008-259451 | 10/2008 |
| WO | WO 2009/065778 | 5/2009 |
| WO | WO 2010/003728 | 1/2010 |

OTHER PUBLICATIONS

Calik et al., Product and by-product distributions in glutamic acid fermentation by *Brevibacterium flavum*: effects of oxygen transfer. Biochemical Engineering Journal vol. 9 (2001) pp. 91-101.*
International Preliminary Report on Patentability and Written Opinion issued Oct. 11, 2012 in PCT/JP2011/055355.
International Search Report issued Apr. 12, 2011 in PCT/JP2011/055355 filed Mar. 8, 2011.
Hartmut F. Zimmermann, et al.; "Oxygen limitation is a pitfall during screening for industrial strains"; Appl. Microbiol. Biotechnol., 2006, vol. 72, No. 6, pp. 1157-1160.
Guezide Calik, et al.; "Product and by-product distributions in glutamic acid fermentation by *Brevibacterium flavum*: effects of the oxygen transfer"; Biochemical Engineering Journal, 2001, vol. 9, No. 2, pp. 91-101.
Yohei Shinfuku, et al.; "Development and experimental verification of a genome-scale metabolic model for *Corynebacterium glutamicum*"; Microbial Cell Factories, 2009, vol. 8:43, pp. 1-15.
Chinese Office Action issued on Aug. 26, 2013, in corresponding application No. 201180011827.7 with English translation.

* cited by examiner

*Primary Examiner* — Ruth Davis
*Assistant Examiner* — Kara Johnson
(74) *Attorney, Agent, or Firm* — Oblon, Spivak, McClelland, Maier & Neustadt, L.L.P.

(57) ABSTRACT

Provided is a method of producing succinic acid in which a microorganism having a succinic acid-producing ability is allowed to react with a sugar, the method being characterized in that the ratio of the oxygen transfer rate to the succinic acid production rate (mmol-$O_2$/mol-SA) is 0.1 to 240 and that the doubling time of the microorganism during the reaction is not shorter than 40 hours.

17 Claims, No Drawings

METHOD OF PRODUCING SUCCINIC ACID

TECHNICAL FIELD

The present invention relates to a method of producing succinic acid using a microorganism having succinic acid-producing ability.

BACKGROUND ART

Production of succinic acid by fermentation is generally carried out under aerobic conditions where a sufficient amount of oxygen is supplied, under microaerobic conditions where a small amount of oxygen is supplied, or under anaerobic conditions where no oxygen is supplied. So far, it has been stated that fermentation reaction under microaerobic conditions or anaerobic conditions is more effective in producing succinic acid as compared to a fermentation reaction under aerobic conditions (Patent Documents 1 to 4 and Non-patent Document 1). In particular, based on the simulation (FBA model) results obtained by using a Coryneform bacteria (*Corynebacterium glutamicum* ATCC 13032), it is stated that the production of succinic acid is improved in conditions where a trace amount of oxygen is supplied than in anaerobic conditions and that the production of succinic acid is further improved by deleting the LDH gene (Non-patent Document 1).

Patent Documents 5 and 6 describe that, in the production of succinic acid using an eukaryotic cell of yeast, *Aspergillus* fungus or the like, the oxygen consumption rate (transfer rate) is controlled at not higher than 0.01 to 5 mmol/L/hr under an oxygen-deficient condition; and that, when oxygen supply is controlled by performing aeration (oxygen limited condition), the oxygen consumption rate is controlled at 5.5 to 7 mmol/L/hr.

PRIOR ART DOCUMENTS

Patent Documents

Patent Document 1: JP 2004-194570A
Patent Document 2: JP 2006-6344A
Patent Document 3: JP 2005-95169A
Patent Document 4: WO2005/026349
Patent Document 5: WO 2009/065778
Patent Document 6: WO 2010/003728

Non-Patent Document

Non-patent Document 1: Shinfuku et al., Development and experimental verification of a genome-scale metabolic model for *Corynebacterium glutamicum*. Microbial Cell Factories 2009, vol. 8: 43

SUMMARY OF THE INVENTION

However, in the simulation (FBA model) described in Non-patent Document 1, calculations are targeted to a condition where the most favorable cell growth is attained; therefore, under the conditions used therein, material sugars are metabolized and used for cell growth, and lactic acid is mainly produced as a metabolite by microbial cells (maximum carbon yield of 60%) and the maximum carbon yield in terms of succinic acid is about 20%. Further, in the production of succinic acid under microaerobic conditions and anaerobic conditions, at oxygen uptake rate (OUR)/sugar uptake rate (GUR) of 0.21, the simulation calculated the carbon yield to be 19.2% while a carbon yield of 3.1% was obtained in the example; thus, there was a discrepancy between the results of the simulation and those of the examples. Therefore, in a condition where cell growth is restricted, the details of the relationship between the oxygen supply to fermentation reaction performed by a microorganism producing succinic acid and the succinic acid-producing reaction have not yet been clarified.

Further, since the cell growth rate is high under the fermentation conditions of the simulation, in a condition where cell growth is restricted, the details of the relationship between the oxygen supply to fermentation reaction and the succinic acid-producing reaction have not yet been clarified.

Moreover, in the case of an industrial-scale production, it is required that the condition be controlled to provide an anaerobic environment where no oxygen is supplied, and specifically, as described in Patent Document 1 and the like, the gasses dissolved in aqueous reaction solution are removed by decompression and oxygen is removed from the reaction system using nitrogen or the like. However, these are not preferred from the standpoint of industrial application since it is enormously costly to, for example, expand the decompression equipment for removal of dissolved gasses and control the nitrogen gas supply. Further, in cases where removal of oxygen from reaction system is performed at an industrial scale, since it takes a very long time before starting the reaction, the conditions of the microbial cells to be used, culture medium and the like are changed, so that there may arise a problem in the reaction itself. In addition, in the industrial-scale production of succinic acid, the relationship between oxygen supply and succinic acid production efficiency has not yet been clarified.

Therefore, an object of the present invention is to provide a succinic acid production method whose production efficiency is higher as compared to conventional methods, particularly, a succinic acid production method which is applicable at an industrial scale.

In order to solve the above-described problems, the present inventors intensively studied and found that, in the production of succinic acid from a raw sugar using a microorganism having succinic acid-producing ability, the production efficiency is improved by controlling the ratio of the oxygen transfer rate to the succinic acid production rate in a specific range under a condition where the growth of the microorganism is restricted, that is, by performing the succinic acid-producing reaction in an environment where a very small amount of oxygen is supplied, thereby completed the present invention.

[1] A method of producing succinic acid, comprising allowing a microorganism having a succinic acid-producing ability to react with a sugar, wherein the ratio of oxygen transfer rate to succinic acid production rate (mmol-O$_2$/mol-SA) is 0.1 to 240 and doubling time of said microorganism during reaction is not shorter than 40 hours.

[2] The method according to [1], wherein percent decrease in oxygen transfer rate with respect to succinic acid (%/g/L) in said reaction is not higher than 1.2.

[3] The method according to [1] or [2], wherein said oxygen transfer rate (mmol-O$_2$/L/hr) in said reaction is 0.01 to 5.

[4] The method according to any one of [1] to [3], wherein said microorganism is selected from the group consisting of coryneform bacteria, *Escherichia coli*, bacteria belonging to the genus *Anaerobiospirillum*, bacteria belonging to the genus *Actinobacillus*, filamentous fungi and yeasts.

[5] The method according to any one of [1] to [4], wherein said microorganism has been modified so that lactate dehydrogenase activity is reduced as compared to an unmodified strain and/or pyruvate carboxylase activity is enhanced as compared to an unmodified strain.

[6] The method according to any one of [1] to [5], wherein pH during said reaction is 5 to 10.

[7] A method of producing a succinic acid-containing polymer, comprising producing succinic acid by the method according to any one of [1] to [6]; and performing polymerization reaction using the resulting succinic acid.

[8] A method of producing a succinic acid derivative, comprising producing succinic acid by the method according to any one of [1] to [6]; and synthesizing a succinic acid derivative using the resulting succinic acid as a starting material.

EMBODIMENTS FOR CARRYING OUT THE INVENTION

Embodiments of the present invention will now be described in detail.

The constituents described below are provided as an example (representative example) of embodiments of the present invention, and these constituents are not restricted to the followings within the scope of the present invention.

Summary of the Present Invention

The present invention is a method of producing succinic acid in which a microorganism having succinic acid-producing ability is allowed to react with a sugar, wherein the ratio of the oxygen transfer rate to the succinic acid production rate (mmol-$O_2$/mol-SA) is in the range of 0.1 to 240 and the doubling time of the microorganism during the reaction is not shorter than 40 hours.

Microorganism

The microorganism to be used in the method of the present invention is not restricted as long as it has succinic acid-producing ability.

In the present invention, the term "succinic acid-producing ability" refers to an ability of a microorganism to accumulate succinic acid in a culture medium when the microorganism is cultured in the medium. Specifically, although not particularly restricted, the level of the succinic acid-producing ability can be indicated by, for example, the carbon yield against consumed sugar.

The carbon yield of succinic acid against consumed sugar (C-mol %) is not particularly restricted; however, when it is too low, the efficiency of the succinic acid production with respect to the material sugar tends to be low as well; therefore, the carbon yield against consumed sugar is usually not less than 40 C-mol %, preferably not less than 50 C-mol %, more preferably not less than 60 C-mol %. On the other hand, the carbon yield against consumed sugar is usually not higher than 133 C-mol %, preferably not higher than 120 C-mol %, more preferably not higher than 110 C-mol %. It is noted here that the term "carbon yield of succinic acid against consumed sugar (C-mol %)" refers to a ratio of the number of moles of carbon atoms contained in the produced succinic acid with respect to the number of moles of carbon atoms contained in the consumed sugar.

The microorganism to be used in the method of the present invention is not particularly restricted as long as it has succinic acid-producing ability, and examples thereof include those microorganisms selected from the group consisting of coryneform bacteria, *Escherichia coli*, bacteria belonging to the genera *Anaerobiospirillum* and *Actinobacillus*, filamentous fungi and yeasts. Thereamong, coryneform bacteria, *Escherichia coli*, bacteria belonging to the genera *Anaerobiospirillum* and *Actinobacillus* and yeasts are preferred and coryneform bacteria, *Escherichia coli* and yeasts are more preferred, and particularly preferred are coryneform bacteria.

Examples of the coryneform bacterium used in the method of the present invention include those belonging to the genera *Corynebacterium*, *Brevibacterium*, *Arthrobacter*, *Mycobacterium*, *Microbacterium* and *Micrococcus*.

As the bacterium belonging to the genus *Brevibacterium*, for example, *Brevibacterium flavum*, *Brevibacterium lactofermentum* or *Corynebacterium glutamicum* is employed.

It is noted here that *Brevibacterium flavum*, *Brevibacterium lactofermentum* and *Corynebacterium glutamicum* are very closely related to each other and have similar characteristics, so that they may be classified into the same species under the current taxonomy.

Particularly preferred specific examples of the parent strain of the coryneform bacterium include *Brevibacterium flavum* MJ-233 (FERM BP-1497), *Brevibacterium flavum* MJ-233 AB-41 (FERM BP-1498), *Corynebacterium glutamicum* ATCC31831 and *Brevibacterium lactofermentum* ATCC13869.

It is noted here that, since *Brevibacterium flavum* is currently be classified as *Corynebacterium glutamicum* (Lielbl, W., et al., International Journal of Systematic Bacteriology, 1991, vol. 41, p255-260), in the present invention, the *Brevibacterium flavum* MJ-233 strain and its mutant strain, MJ-233 AB-41 strain, are regarded as the same as *Corynebacterium glutamicum* MJ-233 strain and *Corynebacterium glutamicum* MJ-233 AB-41 strain, respectively.

*Brevibacterium flavum* MJ-233 has been deposited as of Apr. 28, 1975, with National Institute of Bioscience and Human Technology, Agency of Industrial Science and Technology, Ministry of International Trade and Industry (currently, International Patent Organism Depositary, National Institute of Advanced Industrial Science and Technology; Tsukuba Central 6, 1-1-1 Higashi, Tsukuba, Ibaraki 305-8566, Japan) under the accession No. FERM P-3068, and converted to an international deposit under the accession No. FERM BP-1497 as of May 1, 1981, under the Budapest Treaty.

As the bacterium belonging to the genus *Anaerobiospirillum*, for example, *Anaerobiospirillum succiniciproducens* is employed.

As the bacterium belonging to the genus *Actinobacillus*, for example, *Actinobacillus succinogenes* is employed.

Examples of the filamentous fungi include those belonging to the genera *Aspergillus*, *Penicillium* and *Rhizopus*.

As the microorganism belonging to the genus *Aspergillus*, for example, *Aspergillus niger* or *Aspergillus oryzae* is employed.

As the microorganism belonging to the genus *Penicillium*, for example, *Penicillium chrysogenum* or *Penicillium simplicissimum* is employed.

As the microorganism belonging to the genus *Rhizopus*, for example, *Rhizopus oryzae* is employed.

Examples of the yeasts include those belonging to the genera *Saccharomyces*, *Schizosaccharomyces*, *Candida*, *Pichia*, *Kluyveromyces* and *Zygosaccharomyces*.

As the microorganism belonging to the genus *Saccharomyces*, for example, *Saccharomyces cerevisiae*, *S. uvarum* or *S. bayanus* is employed.

As the microorganism belonging to the genus *Schizosaccharomyces*, for example, *Schizosaccharomyces pombe* is employed.

As the microorganism belonging to the genus *Candida*, for example, *Candida albicans, C. sonorensis* or *C. glabrata* is employed.

As the microorganism belonging to the genus *Pichia*, for example, *Pichia pastoris* or *P. stipitis* is employed.

As the microorganism belonging to the genus *Kluyveromyces*, for example, *Kluyveromyces lactis, K. marxianus* or *K. thermotolerans* is employed.

As the microorganism belonging to the genus *Zygosaccharomyces*, for example, *Zygosaccharomyces bailii* or *Z. rouxii* is employed.

The microorganism to be used in the present invention may have the above-described succinic acid-producing ability as a characteristic of a wild-type strain or may be imparted with the ability by breeding.

In order to impart succinic acid-producing ability, although the method therefor is not particularly restricted, specifically, a conventionally used breeding method of a microorganism, for example, a method of obtaining a mutant strain by a conventional mutation treatment such as UV irradiation or NTG treatment or a method of obtaining a recombinant induced by a genetic technique such as cell fusion or genetic recombination, may be employed.

As the above-described recombinant, one which is obtained by a known method, for example, by enhancing the expression of a succinic acid biosynthetic enzyme gene or down-regulating the expressions of a succinic acid catabolic enzyme gene and by-product biosynthesis gene, may be used. The recombinant to be used in the method of the present invention may be one which has a single modification or one which has two or more modifications. Specific examples thereof include a microorganism which has been modified so that the pyruvate carboxylase activity is enhanced as compared to an unmodified strain and a microorganism which has been modified such that the lactate dehydrogenase activity is reduced as compared to an unmodified strain.

The microorganism which has been modified so that the pyruvate carboxylase (hereinafter, also referred to as "PC" or "pc") activity is enhanced as compared to an unmodified strain can be constructed by, for example, allowing the pc gene to be highly expressed by a plasmid in a host microorganism in the same manner as the method described in JP 11-196888A. Also, the pc gene may be incorporated into the chromosome by homologous recombination, or the expression of the pc gene can be enhanced by promoter substitution (JP 2008-259451A). Further, transformation can be performed by, for example, an electric pulse method (Res. Microbiol., Vol. 144, p. 181-185, 1993).

The phrase "the PC activity is enhanced" used herein means that the PC activity is increased by preferably not less than 1.5 times, more preferably not less than 3.0 times per unit weight of cells, as compared to that of an unmodified strain such as wild-type strain or parent strain. An enhancement of the PC activity can be verified by measuring the PC activity using a known method such as the one described in J. Bacteriol., 158, 55-62 (1984). As a specific introduction method of the pc gene, the one described in JP 2008-259451A can be employed.

Further, the microorganism which has been modified so that the lactate dehydrogenase (hereinafter, may be referred to as "LDH") activity is reduced as compared to an unmodified strain can be constructed by disrupting the LDH gene on the chromosome in accordance with, for example, the homologous recombination method described in JP 11-206385 or the method using sacB gene (Schafer, A. et al., Gene 145 (1994) 69-73). Here, the phrase "the LDH activity is reduced" means that the LDH activity is reduced as compared to an unmodified strain. The LDH activity may be completely eliminated as well. A reduction in the LDH activity can be verified by measuring the LDH activity in accordance with a known method (for example, L. Kanarek, et al., J. Biol. Chem. 239, 4202 (1964)).

Further, the microorganism to be used in the production method according to the present invention may also be one which has been modified such that the activities of one or more enzymes selected from the group consisting of acetate kinase (hereinafter, also referred to as "ACK"), phosphotransacetylase (hereinafter, also referred to as "PTA"), pyruvate oxidase (hereinafter, also referred to as "POXB") and CoA transferase (hereinafter, also referred to as "CTF") are reduced in addition to the above-described enhancement of the PC activity and/or the reduction of the LDH activity.

The activity of only either one of PTA and ACK may be reduced; however, in order to efficiently reduce the by-production of acetic acid, it is more preferred to reduce the activities of both enzymes.

The term "PTA activity" refers to an activity to catalyze a reaction in which phosphate is transferred to acetyl-CoA to generate acetyl phosphate. The phrase "modified so that the PTA activity is reduced" means that the PTA activity is lower than that of an unmodified strain such as wild-type strain. The PTA activity is reduced to preferably not higher than 30%, more preferably not higher than 10% per unit weight of microbial cells, as compared to that of an unmodified strain. Further, the PTA activity may be completely eliminated as well. A reduction in the PTA activity can be verified by measuring the PTA activity in accordance with the method described in Klotzsch, H. R., Meth. Enzymol. 12, 381-386 (1969) or the like.

The term "ACK activity" refers to an activity to catalyze a reaction in which acetic acid is produced from acetyl phosphate and ADP.

The phrase "modified so that the ACK activity is reduced" means that the ACK activity is lower than that of an unmodified strain such as wild-type strain. The ACK activity is reduced to preferably not higher than 30%, more preferably not higher than 10% per unit weight of microbial cells, as compared to that of an unmodified strain. Further, the ACK activity may be completely eliminated as well. A reduction in the ACK activity can be verified by measuring the ACK activity in accordance with the method of Ramponi et al. (Ramponi G., Meth. Enzymol. 42, 409-426 (1975)).

It is noted here that, in *Corynebacterium glutamicum* (including those bacteria classified as *Brevibacterium flavum*), as described in Microbiology. 1999 Feb; 145 (Pt 2): 503-13, since both the PTA and ACK enzymes are encoded by the pta-ack operon (GenBank Accession No. X89084), their activities can be reduced by disrupting the pta gene.

The activities of PTA and ACK can be reduced by disrupting the genes thereof in accordance with a known method, for example, a method using homologous recombination or a method using sacB gene (Schafer, A. et al., Gene 145 (1994) 69-73). Specifically, it can be carried out in accordance with the method disclosed in JP 2006-000091A. As the pta and ack genes, besides the above-described gene having the nucleotide sequence of GenBank Accession No. X89084, a gene having a homology at such a level to allow homologous recombination with the pta and ack genes on the host chromosome can also be used. Here, the "homology at such a level to allow recombination" is preferably not less than 80%, more preferably not less than 90%, particularly preferably not less than 95%. Furthermore, homologous recombination may occur between any DNAs as long as they can hybridize with the above-described genes under stringent conditions.

The term "POXB activity" refers to an activity to catalyze a reaction in which acetic acid is produced from pyruvic acid and water. The phrase "modified so that the POXB activity is reduced" means that the POXB activity is lower than that of an unmodified strain such as wild-type strain. The POXB activity is reduced to preferably not higher than 30%, more preferably not higher than 10% per unit weight of microbial cells, as compared to that of an unmodified strain. The term "reduction" also encompasses a case where the activity is completely eliminated. The POXB activity can be verified by measuring it in accordance with the method described in Chang Y., et al., J. Bacteriol. 151, 1279-1289 (1982) or the like.

The POXB activity can be reduced by disrupting the poxB gene in accordance with a known method, for example, a method using homologous recombination or a method using sacB gene (Schafer, A. et al., Gene 145 (1994) 69-73). Specifically, it can be carried out in accordance with the method disclosed in WO2005/113745 or the like. Examples of the poxB gene include a gene having the nucleotide sequence of GenBank Accession No. Cg12610 (a complementary strand of the 2776766th to 2778505th nucleotides of GenBank Accession No. BA000036); however, any homologous gene of the above-described sequence can also be used as long as it has a homology at such a level to allow homologous recombination with the poxB gene on the chromosomal DNA of the host microorganism. Here, the "homology at such a level to allow homologous recombination" is preferably not less than 80%, more preferably not less than 90%, particularly preferably not less than 95%. Furthermore, homologous recombination may occur between any DNAs as long as they can hybridize with the above-described gene under stringent conditions.

The term "CTF activity" refers to an activity to catalyze a reaction in which CoA of acetyl-CoA is transferred to other substance to generate acetic acid. The phrase "modified so that the CTF activity is reduced" means that the CTF activity is lower than that of an unmodified strain such as wild-type strain. The CTF activity is reduced to preferably not higher than 30%, more preferably not higher than 10% per unit weight of microbial cells, as compared to that of an unmodified strain. The term "reduction" also encompasses a case where the activity is completely eliminated. The CTF activity can be verified by measuring it in accordance with the method described in Scherf U. and Buckel W. Appl. Environ. Microbiol. 1991; vol. 57, pp. 2699-2702 or the like.

Examples of ctf gene include a gene having the nucleotide sequence of GenBank Accession No. Cg12569 (a complementary strand of the 2729376th to 2730917th nucleotides of GenBank Accession No. BA000036); however, any homologous gene of the above-described sequence can also be used as long as it has a homology at such a level to allow homologous recombination with the ctf gene on the chromosomal DNA of the host microorganism. Here, the "homology at such a level to allow recombination" is preferably not less than 80%, more preferably not less than 90%, particularly preferably not less than 95%. Furthermore, homologous recombination may occur between any DNAs as long as they can hybridize with the above-described gene under stringent conditions.

It is noted here that the microorganism to be used in the production method according to the present invention may also be a microorganism obtained by performing two or more of the above-described modifications in combination in addition to the above-described enhancement of the PC activity, or the enhancement of the PC activity and reduction of the LDH activity. Examples of preferred microorganism include the *Brevibacterium flavum* MJ233/PC-4/ΔLDH strain described in JP 2008-259451A and the like; and SUC-200 (MATA ura3-52 leu2-112 trp1-289 adh1::lox adh2::lox gpd1::Kan-lox, overexpressing PCKa, MDH3, FUMR, FRDg and SpMAE1) described in, for example, WO2009/065777, WO2009/065778, WO2009/065779, WO2009/065780 and WO2010/003728, which is a yeast strain in which disruptions of the ADH1 and ADH2 genes encoding alcohol dehydrogenase, disruption of the GPD1 gene encoding glycerol-3-phosphate dehydrogenase and enhancements of phosphoenolpyruvate carboxylase activity, malate dehydrogenase activity, fumarase activity, fumarate reductase activity and malate transporter activity are combined.

Culture

In the present invention, the term "culture" mainly refers to a step of growing the microorganism for to preparing cells thereof to be used for succinic acid production. The culturing step may be omitted, or the microorganism may be cultured on a solid slant medium such as agar medium and directly used for the reaction. Also, alternatively, the culturing step may be repeated several times.

In the present invention, the step of mainly producing succinic acid is referred to as "succinic acid-producing reaction" or "reaction", and the step of culturing to prepare microbial cells to be directly subjected to the succinic acid-producing reaction is referred to as "main culture". Further, culturing to prepare microbial cells to be subjected to the main culture is referred to as "seed culture".

The culture medium to be used for the culture may be any conventional culture medium used for culturing the above-described microorganisms. For example, a common culture medium which is prepared by adding natural nutrient sources, such as meat extract, yeast extract and peptone, to a composition composed of inorganic salts such as ammonium sulfate, potassium phosphate and magnesium sulfate can be employed.

The culture conditions for growing the above-described microorganism to be used in the present reaction to obtain cells thereof are not restricted; however, in cases where a coryneform bacterium is used, although the optimum growth temperature thereof is not particularly restricted, culture thereof is performed at a temperature of usually not lower than 25° C., and usually not higher than 35° C., preferably not higher than 32° C., particularly preferably not higher than 30° C. The culture is performed with aeration, stirring and oxygen supply. Here, the term "optimum growth temperature" refers to a temperature at which the fastest growth rate is attained under the conditions used in the production of succinic acid.

The culture time is not particularly restricted as long as a certain amount of microbial cells are obtained; however, it is usually 6 to 96 hours.

Further, as a method of preparing microbial cells more suitable for the production of succinic acid, the method described in JP 2008-259451A, in which culture is performed by alternately repeating depletion and replenishment of carbon source at short intervals, can also be employed.

After the culture, the resulting culture medium containing the microorganism may be directly used for the succinic acid-producing reaction, or the resulting microbial cells may be recovered by centrifugation or membrane separation and then used for the reaction. As the microorganism to be used in the production method according to the present invention, treated cells thereof may also be employed. Examples of the treated cells include immobilized cells prepared by performing the culture and recovery in accordance with the above-described method and then immobilizing the thus recovered cells with acrylamide, carrageenan or the like; a lysate prepared by lysing the cells; a centrifugation supernatant thereof; and fractions obtained by partially purifying the supernatant with ammonium sulfate or the like.

Sugar to be Used for Culture

In the culture, a sugar is normally used. The sugar to be used for the culture is not particularly restricted as long as it can be assimilated by the above-described microorganism to produce succinic acid; however, usually, a fermentable carbohydrate, for example, a carbohydrate such as galactose, lactose, glucose, fructose, glycerol, sucrose, saccharose, starch or cellulose, or a polyalcohol such as glycerin, mannitol, xylitol or ribitol, is used. Thereamong, glucose, sucrose, fructose or glycerol is preferably used, and glucose or sucrose is particularly preferably used.

Further, a saccharified starch solution, molasses or the like, which contains the above-described fermentable carbohydrate, may also be used, and specifically, a sugar solution obtained from a plant such as sugarcane, sugar beet or sugar maple is preferred.

These sugars may be used individually or in combination. The concentration at which the above-described sugar is used is not particularly restricted; however, it is advantageous to increase the concentration as much as possible within the range in which the production of succinic acid is not inhibited.

The concentration of the above-described sugar is, with respect to the reaction solution, usually not lower than 5% (WN), preferably not lower than 10% (WN), and usually not higher than 30% (W/V), preferably not higher than 20% (WN). Further, the above-described sugar may also be further added in response to a decrease thereof due to the progression of the reaction.

Succinic Acid-Producing Reaction

In the method of producing succinic acid in which the microorganism having succinic acid-producing ability is allowed to react with the sugar, the ratio of the oxygen transfer rate to the succinic acid production rate (mmol-$O_2$/mol-SA) is in the range of 0.1 to 240 and the doubling time of the microorganism during the reaction is not shorter than 40 hours.

Oxygen Transfer Rate

In the present invention, the oxygen transfer rate is not particularly restricted as long as the ratio thereof to the later-described succinic acid production rate is in the above-described range, and the reaction may be performed in an anaerobic atmosphere where no oxygen is supplied to the reaction vessel (a condition in which the oxygen transfer rate is 0). Here, such an anaerobic atmosphere where no oxygen is supplied to the reaction vessel (a condition in which the oxygen transfer rate is 0) can be attained by, for example, a method in which the reaction is performed in a closed container with no aeration, a method in which the reaction is performed with supply of an inert gas such as nitrogen gas or a method in which the reaction vessel is aerated with a carbon dioxide gas-containing inert gas; however, there are problems of, for example, a decrease in the yield of succinic acid and the succinic acid production rate; an increase in the purification cost of succinic acid due to an increase in the generation of by-products such as pyruvic acid; and an increase in the cost for replacing the atmosphere of the reaction vessel with nitrogen or oxygen-free inert gas so as to attain the oxygen transfer rate of 0.

Meanwhile, when the oxygen transfer rate is excessively high, there may also arise problems of, for example, a decrease in the carbon yield of succinic acid against consumed sugar; a decrease in the succinic acid production rate; an increase in the purification cost of succinic acid due to an increase in the generation of acetic acid, which is a by-product; and an increase in the power cost associated with increasing the stirring rate and/or aeration rate so as to attain a high oxygen transfer rate; therefore, the oxygen transfer rate is usually not lower than 0.01 [mmol $O_2$/L/hr], preferably not lower than 0.02 [mmol $O_2$/L/hr], more preferably not lower than 0.05 [mmol $O_2$/L/hr], and usually not higher than 5 [mmol $O_2$/L/hr], preferably not higher than 3 [mmol $O_2$/L/hr], more preferably not higher than 2.5 [mmol $O_2$/L/hr], particularly preferably not higher than 2 [mmol $O_2$/L/hr].

In the present invention, the oxygen transfer rate in the reaction solution can be determined by, for example, a method in which, after subjecting a solution to nitrogen substitution to reduce the dissolve oxygen concentration, the resulting solution is aerated and stirred to determine the oxygen transfer rate based on the changes in the dissolved oxygen concentration (Wise W. S., J. Gen. Microbiol., 1951, vol. 5, pp. 167-1'77).

In the present invention, the method of supplying oxygen to the reaction vessel is not particularly restricted, and for example, an aeration method and a method in which oxygen is dissolved in the reaction solution can also be employed. Preferably, an aeration method is employed. Further, the reaction solution may also be stirred as appropriate such that the oxygen transfer rate is controlled in the above-described range. In order to control the oxygen transfer rate in the above-described range, oxygen may be dissolved by simply stirring the reaction solution, or the reaction solution may be stirred and aerated, or oxygen may be dissolved by aeration alone as well. In addition, a baffle plate may also be installed so as to efficiently generate turbulence by stirring.

In the present invention, the aeration method is not particularly restricted, and examples thereof include bringing the reaction solution or feed solution into contact with an oxygen-containing gas. In order to control the oxygen transfer rate in the above-described range, pure oxygen or an oxygen-containing gas, such as air, may be used as it is, or they may be used in combination. Further, pure oxygen or an oxygen-containing as, such as air, may also be arbitrarily mixed with a gas such as nitrogen or carbon dioxide. Moreover, a gas used once may be recovered and used again. In order to control the oxygen transfer rate in the above-described range, an oxygen-containing gas may be passed through the gas-phase of the reaction vessel via a sparger (aeration tube), such as an orifice sparger, nozzle sparger or ring sparger, or a porous tube by a compressor capable of adjusting the aeration amount, or the reaction solution may be directly aerated with an oxygen-containing gas as well. Further, in order to control the oxygen transfer rate in the above-described range, oxygen may also be indirectly added by dissolving oxygen in the feed solution to be fed during the reaction and feeding this feeding solution to the reaction solution. In cases where the reaction solution, feed solution or the like is aerated, a gas may be directly passed through the solution from a pipe or the like. Alternatively, aeration may be performed using an air diffuser such as a sparger, or a gas may be provided through a membrane or the like. In order to control the oxygen transfer rate in the above-described range, one of the flow rate, pressure and composition of the aerated gas or discharged gas, the oxygen concentration and redox potential of the reaction solution or feed solution, the flow rate of the feed solution and the like may be measured and adjusted as well.

Succinic Acid Production Rate

In the present invention, the term "succinic acid production rate" (mmol/L/hr) refers to an amount of succinic acid produced per 1 L of reaction solution in 1 hour. When the succinic acid production rate is excessively low, the cost tends to be increased because a longer reaction time is required and the yield of succinic acid tends to be decreased due to an increase in the generation of by-products other than succinic acid; therefore, the succinic acid production rate is usually not lower than 1 mmol/L/hr, preferably not lower than 5 mmol/L/hr. Although there is no restriction on the upper limit of the succinic acid production rate, it is usually not higher than 1.000 mmol/L/hr, preferably not higher than 700 mmol/L/hr, more preferably not higher than 300 mmol/L/hr.

Ratio of Oxygen Transfer Rate to Succinic Acid Production Rate

In the present invention, when the ratio of the oxygen transfer rate to the succinic acid production rate (mmol-$O_2$/mol-SA) is excessively small, the amount of the oxygen supply becomes less than a level appropriate for the production of succinic acid, so that there arise problems of, for example, a decrease in the yield of succinic acid; a decrease in the succinic acid production rate; an increase in the purification cost of succinic acid due to an increase in the generation of by-products such as pyruvic acid; and an increase in the cost associated with, for example, replacement of the atmosphere of the reaction vessel with nitrogen which is carried out to realize the required condition of an extremely low oxygen transfer rate; therefore, the ratio of the oxygen transfer rate to the succinic acid production rate is not less than 0.1, preferably not less than 0.2, more preferably not less than 0.3. Meanwhile, when this ratio is excessively large, the amount of the oxygen supply becomes greater than a level appropriate for the production of succinic acid, so that there arise problems of, for example, a decrease in the yield of succinic acid; a decrease in the succinic acid production rate; an increase in the purification cost of succinic acid due to an increase in the generation of acetic acid, which is a by-product; an increase in the generation of by-products in association with cell growth caused by an increased oxygen transfer rate; and an increase in the cost due to a prolonged reaction time caused by a decrease in the succinic acid production rate. Therefore, the ratio of the oxygen transfer rate to the succinic acid production rate is not more 240, preferably not more than 200, more preferably not more than 150, still more preferably not more than 100, particularly preferably not more than 50.

The reason for using the ratio of the oxygen transfer rate to the succinic acid production rate as an index is considered as follows. Conventionally, in succinic acid-producing reaction, in order to maximize the yield of succinic acid, it has been considered theoretically preferable to perform the reaction in an anaerobic environment where the growth rate of microorganism is infinitely low and no oxygen is supplied. However, as a result of the present invention, it was shown that, in a succinic acid-producing reaction performed in an anaerobic environment, by-products such as pyruvic acid are produced in large amounts and the yield of succinic acid is thus low; and that, by supplying a trace amount of oxygen, the amounts of by-products are reduced and the yield of succinic acid as well as the succinic acid production rate are improved. In this manner, in the production of succinic acid accompanying generation of by-products, it was revealed that the succinic acid-producing ability is improved under a condition where a trace amount of oxygen is supplied, not under anaerobic conditions which were considered theoretically preferable by only taking the aspect of the succinic acid production into consideration. This means that the succinic acid-producing reaction requires an appropriately controlled oxygen supply. Yet, with only the oxygen transfer rate being used as an index and set in a certain range, for example, if oxygen was supplied in an amount appropriate for attaining a high succinic acid production rate at the time of reaction when the succinic acid production rate is low, the condition of the succinic acid production would become aerobic and, as described in the above, this leads to an increase in the generation of by-products such as acetic acid, which is not preferred. Therefore, it is considered preferable to use the ratio of the oxygen transfer rate to the succinic acid production rate, which represents the amount of oxygen corresponding to the succinic acid production rate, as an index. Accordingly, in the present invention, it is considered important to control the ratio of the oxygen transfer rate to the succinic acid production rate as an index which primarily shows how much oxygen is required for the succinic acid metabolism of the microorganism having a succinic acid-producing ability.

The above-described ratio of the oxygen transfer rate to the succinic acid production rate can be a preferable index particularly when setting the conditions for industrial succinic acid-producing reaction. In industrial production, preferred succinic acid production rate may be selected and changed depending on the raw material cost and the production installation cost. The above-described index can easily adapt to such changes of the conditions and is thus useful.

Doubling Time

In the present invention, the term "doubling time" refers to the time required for the above-described microorganism to double its amount of cells, and it is represented by the following Equation (1) based on the cell concentrations (OD) or dry cell weights at two time points:

$$\text{Doubling time} = \ln(2) \times \frac{T2 - T1}{\ln\left(\frac{X2}{X1}\right)} \qquad (1)$$

In the above Equation (1), T2 and T1 represent two sampling time points, and X1 and X2 represent the cell concentration or dry cell weight corresponding to the two sampling time points.

In the present invention, when the doubling time of the microorganism is excessively short, the amount of the succinic acid produced is reduced because of the utilization of sugars by cell growth and the cost of the succinic acid purification process is increased due to an increase in the amount of by-products that are produced in association with the growth; therefore, the doubling time is not shorter than 40 hours, preferably not shorter than 50 hours, more preferably not shorter than 100 hours. Meanwhile, although the upper limit of the doubling time is not particularly restricted, when the doubling time is excessively long, the succinic acid production tends to be reduced since the cells used as catalyst completely die out; therefore, the doubling time is usually not longer than 500 hours, preferably not longer than 300 hours, more preferably not longer than 200 hours.

A factor to control the doubling time is not particularly restricted, and examples thereof include reaction conditions such as the amount of oxygen supply and temperature; composition of the reaction solution; and genetic modification of the microorganism. The doubling time can be extended, for example, by controlling the oxygen supply to infinitesimal or 0, by controlling the temperature out of the optimum growth temperature range and/or by restricting a part of the reaction culture medium composition, such as the nitrogen source or phosphorus source. Further, with regard to the genetic modification, the doubling time of a coryneform bacterium can be extended by deleting the LDH gene relating to the production of lactic acid, and similarly, the doubling time of a yeast can be extended by, for example, deleting a gene(s) relating to the production of ethanol (for example, deletion of the ADH1 gene (Mol. Cell. Biol. 1986, vol. 6, pp. 70-79), double deletion of the PDC1 and PDC5 genes or triple deletion of the PDC1, PDC5 and PDC6 genes (Hohmann, J. Bacteriol. 1991, vol. 173, pp. 7963-7969)). An extension of the doubling time can be attained because, for one reason, the ATP acquisition efficiency is impaired by the deletion(s) of these genes. Even when only one of these parameters is controlled, the doubling time may change due to fluctuations in other parameters; therefore, in some cases, the doubling time can be regulated by controlling a plurality of these parameters in combination. Specific methods of controlling the above-described parameters, applicable ranges thereof and the like are as described in the respective sections.

Further, when the doubling times in the succinic acid-producing reactions of Reference 1 (Shinfuku et al., Microbial Cell Factories 2009, 8:43) and Reference 2 (WO2010/003728) are calculated in the same manner using the above-described Equation (1), the doubling times in the Reference 1 are 27.4 hours (the ODs were read from the drawing of the Additional File 2 and the doubling time was calculated based on the ODs at the 9th hour (12.2) and 24th hour (17) from the start of the culture) and 7.3 hours (the ODs were read from the drawing of the Additional File 3 and the doubling time was calculated based on the ODs at the 9th hour (6.5) and 25th hour (26) from the start of the culture), and the doubling time in the Reference 2 is 30 hours (this doubling time was calculated using the values described in Examples 1 and 2 of the Reference 2: a biomass dry weight (dry cell weight) of 1 g at the start of the culture and a biomass dry weight (dry cell weight) of 8 g at the 90th hour), all of which doubling times are shorter than 40 hours.

Percent Decrease in Oxygen Transfer Rate with Respect to Succinic Acid

In the present invention, the percent decrease in the oxygen transfer rate with respect to succinic acid (%/g/L) indicates a ratio of a decrease in the oxygen transfer rate during the production of 1 g of succinic acid per 1 L of reaction solution and it is represented by the following Equation (2):

$$\text{percent decrease in the oxygen transfer rate with respect to succinic acid} = \frac{100 \times \left(1 - \frac{OTR_{t2}}{OTR_{t1}}\right)}{SA_{t2} - SA_{t1}} \quad (2)$$

In the above Equation (2), $OTR_{t1}$ and $OTR_{t2}$ represent the oxygen transfer rate (mmol-$O_2$/L/hr) at time t1 after the start of the reaction and the subsequent time t2, respectively, and $SA_{t1}$ and $SA_{t2}$ represent the succinic acid concentration (g/L) of the reaction solution at the time t1 and time t2, respectively. Further, in a continuous reaction involving inflow and outflow of the reaction solution, for example, the $SA_{t1}$ can be calculated as a value of "the total amount of succinic acid (g) contained in the reaction solution removed before the time t1 and the reaction solution in the reaction vessel" with respect to "the amount of the reaction solution (L) in the reaction vessel".

At an arbitrary time in the reaction, the percent decrease in the oxygen transfer rate with respect to succinic acid (%/g/L) is usually not higher than 1.2 (%/g/L), more preferably not higher than 1.1 (%/g/L). The lower limit thereof is not particularly restricted and it may be 0. It is preferred that the percent decrease in the oxygen transfer rate with respect to succinic acid be not higher than 1.2 (%/g/L) since, at such a level, the amount of oxygen can be maintained at a level most appropriate for the production of succinic acid by suppressing a decrease in the oxygen transfer rate, which leads to suppression of a decrease in the yield of succinic acid and the succinic acid production rate, and the purification cost of succinic acid can also be reduced by a resulting reduction in the amount of pyruvic acid generated as a by-product.

The effects of the present invention cannot be attained by controlling only one of the parameters, such as the succinic acid production rate, the oxygen transfer rate or the doubling time of the microorganism. For example, with only the doubling time of the microorganism being controlled to be extended by complete elimination of oxygen, impurities such as lactic acid and acetic acid are produced in large amounts, so that there is a problem of a decrease in the succinic acid production rate. Further, when the oxygen transfer rate is enhanced for the purpose of enhancing the succinic acid-producing reaction, the growth of the microorganism is activated in association with the enhancement of the oxygen transfer rate and the majority of material sugars for succinic acid are thus used by the growth of the microorganism, so that there arises a problem of a decrease in the amount of succinic acid production. The effects of the present invention can be achieved only when a plurality of parameters, such as the succinic acid production rate, the oxygen transfer rate and the doubling time of the microorganism, are controlled in order to improve the yield and production rate of succinic acid.

Temperature and Time of Succinic Acid-Producing Reaction

The temperature of the succinic acid-producing reaction is not particularly restricted; however, it is higher than the optimum growth temperature of the above-described microorganism to be used by usually not less than 2° C., preferably not less than 7° C., and by usually not more than 20° C., preferably not more than 15° C. Specifically, in the case of a coryneform bacterium, the temperature of the succinic acid-producing reaction is usually not lower than 37° C., preferably not lower than 39° C., and usually not higher than 45° C., preferably not higher than 43° C., particularly preferably not higher than 41° C. Although it is not required that the temperature be in the range of 37 to 45° C. throughout the succinic acid-producing reaction, it is desired that the temperature be in the above-described range for not less than 50%, preferably not less than 80% of the entire reaction time including the time of seed culture.

The reaction time is not particularly restricted; however, it is usually not short than 1 hour, preferably not shorter than 3 hours, and usually not longer than 168 hours, preferably not longer than 72 hours.

Method of Preparing Microorganism to be Used in Succinic Acid-Producing Reaction In the production method of succinic acid according to the present invention, succinic acid may be produced by allowing the above-described microorganism to react with a sugar or by allowing microorganism grown by the above-described culture in advance to react with a sugar in a reaction solution containing the sugar. In particular, the latter method is useful mainly because optimum conditions can be selected in each of the steps of growing the microorganism and producing succinic acid and the added sugar can thus be efficiently utilized in the production of succinic acid.

The amount of the above-described microorganism to be used in the succinic acid-producing reaction is not particularly prescribed; however, in terms of the wet cell weight, the above-described microorganism is used in an amount of usually not less than 1 g/L, preferably not less than 10 g/L, more preferably not less than 20 g/L, and usually not more than 700 g/L, preferably not more than 500 g/L, still more preferably not more than 400 g/L.

Sugar to be Used in Succinic Acid-Producing Reaction

The sugar to be used in the succinic acid-producing reaction is the same as the one to be used in the above-described culture.

The concentration at which the sugar is used in the production of succinic acid is not particularly restricted; however, it is advantageous to increase the concentration as much as possible within the range in which the production of succinic acid is not inhibited. The concentration of the sugar is usually not lower than 5% (W/V), preferably not lower than 10% (W/V), and usually not higher than 30% (W/V), preferably not higher than 20% (W/V), in the reaction solution. Further, the sugar may also be further added in response to a decrease thereof due to the progression of the reaction.

Reaction Solution

The reaction solution to be used in the succinic acid-producing reaction of the present invention is not particularly restricted as long as it is an aqueous solution which contains the above-described microorganism and the above-described sugar, and it may be a medium for culturing the above-described microorganism or a buffer solution such as phosphate buffer.

The reaction solution is preferably an aqueous solution containing a nitrogen source, an inorganic salt and the like. Here, the nitrogen source is not particularly restricted as long as it can be assimilated by the above-described microorganism to produce succinic acid or the like, and specific examples of such nitrogen source include a variety of organic and inorganic nitrogen compounds such as ammonium salts, nitrates, urea, soybean hydrolysates, casein digests, peptone, yeast extracts, meat extracts and corn steep liquors. As the inorganic salt, a variety of phosphates, sulfates and metal salts of magnesium, potassium, manganese, iron, zinc and the like may be used. Further, a growth-promoting factor(s) such as vitamins (e.g. biotin, pantothenic acid, inositol and nicotinic acid), nucleotides and amino acids may be added as required. Moreover, in order to suppress foam formation at the time of reaction, it is desirable to add an appropriate amount of a commercially available antifoaming agent to the reaction solution.

It is preferred that the pH of the reaction solution be adjusted according to the type of the above-described microorganism in a range where the activities thereof are most effectively exerted. Specifically, in cases where a coryneform bacterium is used, the pH of the reaction solution is usually not lower than 5, preferably not lower than 5.5, more preferably not lower than 6, particularly preferably not lower than 7.1, and not higher than 10, preferably not higher than 9.5, more preferably not higher than 9.0. The pH of the reaction solution is adjusted as required in the above-described range also during the reaction by adding a neutralizing agent such as alkaline substance, carbonate or urea. Specifically, the pH of the reaction solution can be adjusted by adding, for example, sodium carbonate, sodium bicarbonate, potassium carbonate, potassium bicarbonate, magnesium carbonate, sodium hydroxide, calcium hydroxide or magnesium hydroxide.

It is preferred that the reaction solution also contain a carbonate ion, bicarbonate ion, carbon dioxide gas ($CO_2$) or the like in addition to the above-described microorganism, sugar, nitrogen source and inorganic salt. The carbonate ion or the bicarbonate ion is supplied from magnesium carbonate, sodium carbonate, sodium bicarbonate, potassium carbonate, potassium bicarbonate or the like, which can also be used as a neutralizing agent; however, as required, the ion may also be supplied from carbonic acid or bicarbonic acid, or a salt thereof, or carbon dioxide gas.

Specific examples of the carbonate or bicarbonate include magnesium carbonate, ammonium carbonate, sodium carbonate, potassium carbonate, ammonium bicarbonate, sodium bicarbonate and potassium bicarbonate. Further, the carbonate ion or bicarbonate ion is added at a concentration of usually not lower than 1 mM, preferably not lower than 2 mM, more preferably not lower than 3 mM, and usually not higher than 500 mM, preferably not higher than 300 mM, more preferably not higher than 200 mM. In cases where carbon dioxide gas is added, it is contained in an amount of usually not less than 50 mg, preferably not less than 100 mg, more preferably not less than 150 mg, and usually not more than 25 g, preferably not more than 15 g, more preferably not more than 10 g, per 1 L of the solution.

Other Conditions in Succinic Acid-Producing Reaction

The production method of succinic acid according to the present invention can be controlled by measuring and adjusting, in addition to the above-described items, any of the flow rate, pressure and composition of the aerated gas or discharged gas, the oxygen concentration or redox potential of the reaction solution or feed solution, the flow rate of the feed solution and the like. The production method of the present invention is adjusted in accordance with the type of the microorganism used, the later-described reaction vessel, the method of oxygen supply or the like such that the efficiency of succinic acid production is most effectively achieved. Specifically, in cases where the surface of the reaction solution is aerated in a jar fermentor, although not particularly restricted to the followings, the stirring rate is usually 50 rpm to 2,000 rpm, the amount of aeration with respect to the solution amount is usually 0.001 vvm to 10 vvm, and the amount of air contained in the aeration gas is usually 0.1% to 100%.

The production method according to the present invention can be applied to batch reaction, semi-batch reaction or continuous reaction. In particular, in the case of a reaction in which the above-described neutralizing agent is added, continuous reaction or the like, since the reaction conditions (such as the amount of reaction solution) change sequentially and largely, the ratio of the oxygen transfer rate to the succinic acid production rate often deviates from the optimum condition; however, the method according to the present invention appropriately adjusts using the ratio of the oxygen transfer rate to the succinic acid production rate as an index, thus preferable.

Succinic Acid-Producing Reaction at Industrial Scale

For industrial-scale production of succinic acid by fermentation, a method which has been conventionally used for fermentation of lactic acid, acetic acid, glutamic acid or the like at an industrial scale can be applied (see Bioreaction Engineering (3rd Edition), Sangyo-Tosho Publishing Co., Ltd., p. 266-276).

In industrial-scale fermentation, the type of microorganism reaction vessel and the method of introducing a gas such as oxygen or carbon dioxide are important.

In the present invention, the type of the microorganism reaction vessel is not particularly restricted; however, examples thereof include bubble agitation-type (in which a gas is introduced to a liquid and the gas-liquid contact is facilitated using a stirrer to increase the absorption rate); liquid surface absorption-type (in which a gas is absorbed via the liquid surface); liquid surface absorption and agitation-type (in which a stirrer is installed in a liquid surface absorption-type vessel and used to increase the oxygen absorption rate); external absorption-type (in which a separate device is installed externally to circulate reaction solution for oxygen absorption or a liquid fed during reaction is allowed to absorb oxygen); standard bubble column-type; draft tube-type (in which a draft tube is installed and used to facilitate internal circulation to increase the gas absorption rate—a gas may also be introduced from near the lateral surface of the column such that the gas flows upward in the periphery and downward in the center); draft tube-shaped perforated plate-type (in which a perforated plate is installed in a draft tube-shape to facilitate the gas-liquid contact, thereby increasing the absorption rate); multiple perforated plate-type; and external loop air lift-type (in which a circulation flow channel is installed externally to introduce a gas).

The gas introduction method is not particularly restricted; however, examples thereof include a bubble entrainment-type method using a single-pore nozzle, multi-pore nozzle, ring sparger, multipipe, gas-liquid two-phase flow nozzle or liquid jet.

In the present invention, the term "industrial-scale reaction" is not particularly restricted; however, it is, in terms of the volume of the reaction vessel, usually not smaller than 5 $m^3$, preferably not smaller than 50 $m^3$, and usually not larger than 5,000 $m^3$, preferably not larger than 3,000 $m^3$.

The reasons why the present invention is suitable for industrial-scale reaction include the followings.

In cases where no aeration is provided, oxygen to be supplied to the reaction solution exits only in the gas phase of the reaction vessel; however, at an industrial scale, from the standpoint of improving the reaction vessel capacity, it is preferred that the volume of the gas phase with respect to the reaction vessel be made smaller than that of the small scale such as the below-described examples of the present invention. By doing so, the amount of oxygen would not be enough to maintain an oxygen transfer rate suitable for the reaction and the ratio of the oxygen transfer rate to the succinic acid production rate would thus not be attained in the preferred range; however, the yield of succinic acid can be improved by controlling this ratio within a certain range by controlling aeration and the like according to the production method of the present invention, thus the production method of the present invention is useful.

Further, in industrial reaction, the succinic acid production rate is changed depending on the raw material cost and the production installation cost; however, by using the production method of the present invention, optimum reaction conditions can be easily set.

Post Treatment

By the above-described reaction, succinic acid is produced and accumulated in the reaction solution.

Specific examples of by-products generated in the production process of succinic acid include citric acid cycle metabolites other than succinic acid, such as acetic acid, ethanol, lactic acid, pyruvic acid and $\alpha$-ketoglutaric acid; amino acid precursors such as $\alpha$-ketovaline; amino acids such as alanine, valine and glutamic acid; sugars such as trehalose; alcohols such as glycerol; and proteins.

The amount of the by-products is not particularly restricted; however, specifically, in cases where the by-product is pyruvic acid or acetic acid, the weight ratio (%) of pyruvic acid with respect to succinic acid is usually not higher than 5.5%, preferably not higher than 5.2%, and the weight ratio (%) of acetic acid with respect to succinic acid is, although not particularly restricted, usually not higher than 15.8%, preferably not higher than 15.5%.

The succinic acid accumulated in the reaction solution (culture medium) can be recovered therefrom in accordance with a conventional method. For example, after the reaction by the microorganism, the reaction solution is, in view of the operability and efficiency of the subsequent purification step, concentrated as appropriate and then subjected to centrifugation, filtration or the like to remove solid matters such as microbial cells. In this manner, a solution or an aqueous solution which contains, as major components, succinic acid and a succinate(s) such as ammonium succinate and magnesium succinate can be obtained. The phrase "contain as major components" used herein refers to a condition in which the solution/aqueous solution contains the subject components in an amount of usually not less than 50% by weight, preferably not less than 60%, more preferably not less than 70%, particularly preferably not less than 90%, with respect to the total weight of all the components except the solvent.

Succinic acid can be recovered by, for example, performing purification by crystallization or column chromatography.

Applications of Obtained Succinic Acid

Generally, succinic acid is produced from a material of petrochemical origin and used in a variety of applications; however, succinic acid derived from a biological source can also be used in those applications in the same manner. Such succinic acid can be used as, for example, a starting material of succinic acid derivatives such as succinic acid esters (e.g. 1,4-butanediol, 2-pyrrolidine, succinimide, maleic anhydride, itaconic acid, aspartic acid, maleic acid, fumaric acid, hydroxysuccinimide, maleimide, 4-aminobutyrate, $\gamma$-aminobutyrate, tetrahydrofuran, acrylic acid, dimethyl succinate and diethyl succinate), pyrrolidone and N-methylpyrrolidone; a raw material for succinic acid-containing polymer compounds, products and the like of polyester, polyurethane, polyamide and the like; a food additive such as acidulant, flavoring agent, brewing chemical or processed food additive; a bubble bath component; a synthetic material and component of pharmaceuticals and agricultural chemicals, such as plant growth retardants, herbicides, antibacterial agents, pesticides and mosquito attractants; a raw material and component of mouthwash agents, cosmetics and the like; a raw material and component of those products used in photographs, printing and the like; a material and component of adhesives and sealants, such as high-temperature welding agents and alumite-treated surface adhesives; a material and component used in metal processing such as powder nickel production, steel polishing bath, washing solvent in metal processing and binder for metal sintering; a material and component of solders and welding fluxes; a raw material and component of auxiliary agents used in the production of ceramics, inorganic compounds and the like, such as porous titanium oxide, boehmite, photocatalytic coating agents and porous ceramics; a raw material and component of washing agents and the like; a raw material and component of bleaches and the like; a raw material and component of dyeing auxiliaries; a raw material and component of electrolyte solvents, plating bathes and the like; a raw material and component of deodorizers, air fresheners and the like; a raw material of bioabsorbable compounds such as bioabsorbable surgical sutures; a raw material and component of treatment agents, softeners and the like of textile products; a raw material and component of dispersing agents, solvents and the like; a raw material and component of water-soluble paint solvents; a raw material and component of biodegradable resins; a raw material and component of sealants such as odor-free sealants; a raw material and component of anticorrosive agents used in coating of steel products, copper products and alloy metal products, freeze proofing, metal processing, lead for perchloric acid, boiler water treatment and the like; a raw material and component for synthesizing lubricants such as synthetic lubricants, lubricants for heat-resistant plastics and electrical contact lubricants; a raw material and component of solvent-removing washing agents and the like used for resins, polymer materials and the like; a raw material and component of products used in the textile industry, dry cleaning and the like; a raw material and component of pigments, dyes, inks and the like that are used in, for example, ink solvents, deinking agents, automobile top-coating agents, insulating varnishes, powder paints, three-dimensional printing inks, photosetting-type paints, photosetting ink compositions, nanoparticle inks, ink jet inks, printing screen washing agents, organic semiconductor solutions, inks for color filter production, toners, quinacridone pigment production, succinyl succinate production and dye intermediates; a raw material and component of oxygen-containing-type diesel fuels and the like; a raw material and component of cement admixtures, cement treatment agents and the like; a raw material and component of engine cleaners and the like; a raw material and component of petroleum refinery solvents and the like; a raw material and component of oil and natural gas extraction auxiliary agents such as proppant composition and those used for removal of precipitation filter cake; a raw material and component of those products relating to natural gas production, such as natural gas dehydrating solvents; a raw material and component of construction materials such as low-dust concrete flooring materials and asphalt pavement materials; and a raw material and component of ink solvents and deinking agents.

EXAMPLES

The present invention will now be described more concretely by way of examples thereof; however, the present invention is not restricted thereto and various modifications can be made within the scope of the present invention.

Each of the following analysis items was measured as follows.

<Measurement of Oxygen Transfer Rate>

For the measurement of oxygen transfer rate, a method in which a solution is subjected to nitrogen substitution to reduce the dissolve oxygen concentration and then the resulting solution is aerated and stirred to determine the oxygen transfer rate based on the changes in the dissolved oxygen concentration (Wise W. S., J. Gen. Microbiol., 1951, vol. 5, pp. 167-177) was employed. Specifically, a desired amount of water was placed in a 1-L jar fermentor and the water was then subjected to aeration with nitrogen and stirring to remove the dissolved oxygen. After substituting the gas phase of the jar fermentor by aeration with air, the liquid was aerated with air from the surface or the bottom at an aeration rate of 100 mL/min and simultaneously stirred at 100 rpm to 500 rpm. The oxygen transfer rate was calculated from the subsequent changes in the dissolved oxygen concentration. In addition, by performing aeration with a mixed gas of air and nitrogen, a lower oxygen transfer rate was measured.

<Method of Measuring Succinic Acid, Pyruvic Acid and Acetic Acid>

Succinic acid, pyruvic acid and acetic acid contained in a reaction solution were analyzed by centrifuging the reaction solution (15,000 G, 2 minutes) and subjecting the resulting supernatant to liquid chromatography (LC). The succinic acid production rate (mmol-SA/L/hr) was calculated by dividing the measured succinic acid concentration by sampling time (hr).

<Method of Measuring Doubling Time>

The doubling time was determined using the following Equation (1) based on the cell concentrations (OD) or dry cell weights at two time points:

$$\text{Doubling time} = \ln(2) \times \frac{T2 - T1}{\ln\left(\frac{X2}{X1}\right)} \quad (1)$$

(wherein, T2 and T1 represent two sampling time points; and X1 and X2 represent the dry cell weights corresponding to the two sampling time points).

<Calculation Method of Percent Decrease in the Oxygen Transfer Rate with Respect to Succinic Acid (%/g/L)>

The percent decrease in the oxygen transfer rate with respect to succinic acid (%/g/L) indicates a ratio of a decrease in the oxygen transfer rate during the production of 1 g of succinic acid per 1 L of reaction solution and it was calculated by the following Equation (2):

$$\text{percent decrease in the oxygen transfer rate with respect to succinic acid} = \frac{100 \times \left(1 - \frac{OTR_{t2}}{OTR_{t1}}\right)}{SA_{t2} - SA_{t1}} \quad (2)$$

In the above Equation (2), $OTR_{t1}$ and $OTR_{t2}$ represent the oxygen transfer rate (mmol-$O_2$/L/hr) at time t1 after the start of the reaction and the subsequent time t2, respectively, and $SA_{t1}$ and $SA_{t2}$ represent the succinic acid concentration (g/L) of the reaction solution at the time t1 and time t2, respectively. Further, in a continuous reaction involving inflow and outflow of the reaction solution, for example, the $SA_{t1}$ can be calculated as a value of "the total amount of succinic acid (g) contained in the reaction solution removed before the time t1 and the reaction solution in the reaction vessel" with respect to "the amount of the reaction solution (L) in the reaction vessel".

Example 1

Production of Succinic Acid with Controlled Oxygen Supply
<Seed Culture>

To a 500-mL Erlenmeyer flask, 100 mL of culture medium A (4 g of urea, 14 g of $(NH_4)_2SO_4$, 0.5 g of $KH_2PO_4$, 0.5 g of $K_2HPO_4$, 0.5 g of $MgSO_4.7H_2O$, 20 mg of $FeSO_4.7H_2O$, 20 mg of $MnSO_4.H_2O$, 200 μg of D-biotin, 200 μg of thiamine hydrochloride, 1 g of yeast extract and 1 g of casamino acid in 1,000 mL of distilled water) was loaded and heat-sterilized at 121° C. for 20 minutes. After being cooled to room temperature, 15 mL of the thus sterilized culture medium A was placed in a 200-mL Erlenmeyer flask and added with 600 μL of 50% glucose aqueous solution which had been sterilized in advance. Then, the MJ233/PC/ALDH strain was inoculated and cultured for 5.5 hours at 30° C. In the above-described 500-mL Erlenmeyer flask, 100 mL of the culture medium A was placed and sterilized, and 4 mL of 50% glucose aqueous solution, which had been sterilized in advance, was then added thereto. Thereafter, the resulting culture medium was inoculated such that the O.D. (660 nm) became 0.02, and seed-cultured at 30° C. for 20 hours.
<Main Culture>

A total of 1,833 mL of a culture medium composed of 6.68 g of an aqueous phosphoric acid solution (85 wt %), 4.95 g of KCl, 2.97 g of $(NH_4)_2SO_4$, 1.48 g of $MgSO_4.7H_2O$, 118.8 mg of $MnSO_4.5H_2O$, 118.8 mg of $FeSO_4.7H_2O$, 29.93 g of CSL (corn steep liquor), 11.08 g of 10 N aqueous potassium hydroxide solution, 2.54 g of antifoaming agent (CE457: manufactured by Nippon Oil & Fats Co., Ltd.) and distilled water was placed in a 5-L jar fermentor and heat-sterilized at 121° C. for 20 minutes. After being cooled to room temperature, the resulting culture medium was added with 15 mL of a vitamin solution (D-biotin and thiamine hydrochloride of 0.2 g each/L aqueous solution) which had been filter-sterilized in advance, 110 mL of an aqueous material sugar solution (720 g/L) which had been sterilized in advance and 100 mL of the above-described seed culture solution. Taking into consideration the amount of evaporated medium based on the weight thereof before and after the heat-sterilization, sterilized water was added to a total amount of 2,500 mL. The jar fermentor was incubated at 30° C. and the pH was maintained at 7.2 using 28% aqueous ammonia to start main culture with a back pressure of 0.05 MPa, aeration at 3 L/min and stirring at 600 rpm. The dissolved oxygen concentration decreased to almost 0 and then started to increase again, and at the point when it reached 1 ppm, about 7 g of the material sugar (720 g/L), which had been sterilized in advance, was added. As a result, the dissolved oxygen concentration decreased again to 0. The material sugar solution was repeatedly added in accordance with the above-described method every time the dissolved oxygen concentration increased again and the culture was continued for 19 hours after the start thereof.
<Succinic Acid-Producing Reaction>

After heat-sterilizing 5.2 g of an aqueous phosphoric acid solution (85 wt %), 3.46 g of $MgSO_4.7H_2O$, 138.2 mg of $MnSO_4.5H_2O$, 138.2 mg of $FeSO_4.7H_2O$, 9.14 g of 10 N aqueous potassium hydroxide solution and 105 mL of distilled water at 121° C. for 20 minutes, with consideration of the amount of evaporation by the heat-sterilization, sterilized water was added to the thus heat-sterilized mixture to obtain a solution in an amount of 320 mL. Then, 20 mL of the thus obtained solution, 88 mL of an aqueous material sugar solution (720 g/L), 228.1 mL of sterilized water, 448 μL of a vitamin solution (D-biotin and thiamine hydrochloride of 0.2 g each/L aqueous solution) which had been filter-sterilized in advance and 135 mL of the above-described main culture solution were placed in a 1-L jar fermentor. The pH was maintained at 7.6 using a Na neutralizing agent (113.5 g of sodium bicarbonate, 145.9 g of sodium hydroxide and 936.7 of sterilized water) and the resultant was incubated at 39° C.

The surface of the thus obtained reaction solution was aerated at 100 mL/min with a gas prepared by mixing air and nitrogen such that the air-to-nitrogen amount ratio was 5:95, and the resultant was stirred at 100 rpm. The ratio of the oxygen transfer rate to the succinic acid production rate (mmol-$O_2$/mol-SA), succinic acid production rate (mmol-SA/L/hr), oxygen transfer rate (mmol-$O_2$/L/hr), carbon yield of succinic acid against consumed sugar (C-mol %), percent decrease in the oxygen transfer rate with respect to succinic acid (%/g/L), pyruvic acid-to-succinic acid weight ratio (%) and acetic acid-to-succinic acid weight ratio (%), which were measured after 20 hours of incubation, are shown in Table 1. It is noted here that, although precise doubling time was not measured, assuming from the values obtained in Examples 6, 7 and 9, it is clear that the doubling time was not shorter than 40 hours.

Example 2

Succinic acid was produced in the same manner as in Example 1 except that the air-to-nitrogen amount ratio of the mixed gas used for aeration was changed to 10:90. The results for the above-described items are shown in Table 1. It is noted here that, although precise doubling time was not measured, assuming from the values obtained in Examples 6, 7 and 9, it is clear that the doubling time was not shorter than 40 hours.

Example 3

Succinic acid was produced in the same manner as in Example 1 except that the air-to-nitrogen amount ratio of the mixed gas used for aeration was changed to 14:86. The results for the above-described items are shown in Table 1. It is noted here that, although precise doubling time was not measured, assuming from the values obtained in Examples 6, 7 and 9, it is clear that the doubling time was not shorter than 40 hours.

Example 4

Succinic acid was produced in the same manner as in Example 1 except that the air-to-nitrogen amount ratio of the mixed gas used for aeration was changed to 25:75. The results for the above-described items are shown in Table 1. It is noted here that, although precise doubling time was not measured, assuming from the values obtained in Examples 6, 7 and 9, it is clear that the doubling time was not shorter than 40 hours.

Example 5

Succinic acid was produced in the same manner as in Example 1 except that the air-to-nitrogen amount ratio of the mixed gas used for aeration was changed to 50:50. The results for the above-described items are shown in Table 1. It is noted here that, although precise doubling time was not measured, assuming from the values obtained in Examples 6, 7 and 9, it is clear that the doubling time was not shorter than 40 hours.

Example 6

Succinic acid was produced in the same manner as in Example 1 except that the air-to-nitrogen amount ratio of the mixed gas used for aeration was changed to 100:0 and that the doubling time was calculated using the above-described equation. The results for the above-described items are shown in Table 1 along with the calculated doubling time.

Example 7

Succinic acid was produced in the same manner as in Example 6 except that the stirring was performed at 200 rpm. The results for the above-described items are shown in Table 1.

Example 8

Succinic acid was produced in the same manner as in Example 6 except that the stirring was performed at 400 rpm. The results for the above-described items are shown in Table 1. It is noted here that, although precise doubling time was not measured, assuming from the values obtained in Examples 6, 7 and 9, it is clear that the doubling time was not shorter than 40 hours.

Example 9

Succinic acid was produced in the same manner as in Example 6 except that the stirring was performed at 500 rpm. The results for the above-described items are shown in Table 1.

Comparative Example 1

Succinic acid was produced in the same manner as in Example 1 except that, after substituting the gas phase of the jar fermentor with nitrogen, the air-to-nitrogen amount ratio of the mixed gas for aeration was changed to 0:100 to aerate the surface of the reaction solution and the reaction was carried out with stirring at 200 rpm. The results for the above-described items are shown in Table 1. It is noted here that, although precise doubling time was not measured, it is presumed to be not shorter than 40 hours.

Comparative Example 2

Succinic acid was produced in the same manner as in Example 1 except that the air-to-nitrogen amount ratio of the mixed gas for aeration was changed to 100:1 to aerate the reaction solution from the bottom and the reaction was carried out with stirring at 400 rpm. The results for the above-described items are shown in Table 1. It is noted here that, although precise doubling time was not measured, it is presumed to be not shorter than 40 hours.

TABLE 1

|  |  | Comp. Ex. 1 | Ex. 1 | Ex. 2 | Ex. 3 | Ex. 4 | Ex. 5 | Ex. 6 | Ex. 7 | Ex. 8 | Ex. 9 | Comp. Ex. 2 |
| --- | --- | --- | --- | --- | --- | --- | --- | --- | --- | --- | --- | --- |
| Conditions | Stirring rate (rpm) | 200 | 100 | 100 | 100 | 100 | 100 | 100 | 200 | 400 | 500 | 400 |
|  | Aeration rate (mL/min) | 100 | 100 | 100 | 100 | 100 | 100 | 100 | 100 | 100 | 100 | 100 |
|  | Position of aeration with respect to the surface of the reaction solution | At surface | At surface | At surface | At surface | At surface | At surface | At surface | At surface | At surface | At surface | From the bottom |
|  | Air-to-nitrogen ratio of the aeration gas ($O_2$:$N_2$) | 0:100 | 5:95 | 10:90 | 14:86 | 25:75 | 50:50 | 100:0 | 100:0 | 100:0 | 100:0 | 100:0 |
| Results | Ratio of the oxygen transfer rate to the succinic acid production rate (mmol-$O_2$/mol-SA) | 0 | 0.38 | 0.78 | 1.17 | 2.06 | 6.38 | 9.88 | 31.67 | 59.03 | 105.82 | 250.70 |
|  | Succinic acid production rate (mmol-SA/L/hr) | 24.0 | 26.6 | 26.9 | 26.4 | 25.2 | 25.1 | 24.9 | 24.8 | 24.7 | 24.7 | 23.8 |
|  | Oxygen transfer rate (mmol-$O_2$/L/hr) | 0 | 0.01 | 0.02 | 0.03 | 0.05 | 0.16 | 0.25 | 0.79 | 1.46 | 2.61 | 5.96 |
|  | Carbon yield of succinic acid against consumed sugar (C-mol %) | 78.8% | 79.6% | 80.2% | 80.9% | 81.0% | 81.6% | 82.4% | 81.8% | 81.9% | 81.1% | 79.9% |
|  | Percent decrease in the oxygen transfer rate with respect to succinic acid (%/g/L) | — | 0.63 | 0.63 | 0.63 | 0.63 | 0.65 | 0.78 | 0.92 | 0.81 | 1.02 | 0.46 |

TABLE 1-continued

|  | Comp. Ex. 1 | Ex. 1 | Ex. 2 | Ex. 3 | Ex. 4 | Ex. 5 | Ex. 6 | Ex. 7 | Ex. 8 | Ex. 9 | Comp. Ex. 2 |
|---|---|---|---|---|---|---|---|---|---|---|---|
| Pyruvic acid-to-succinic acid weight ratio (%) | 6.0 | 49 | 4.0 | 3.4 | 3.0 | 2.5 | 2.2 | 2.5 | 2.2 | 1.8 | 1.8 |
| Acetic acid-to-succinic acid weight ratio (%) | 9.9 | 10.3 | 11.6 | 11.2 | 13.1 | 14.0 | 13.8 | 13.7 | 14.5 | 15.3 | 16.2 |
| Doubling time (hr) | — | — | — | — | — | — | 218.5 | 266.6 | — | 205.1 | — |

Example 10

Effects of Controlled Oxygen Supply (Percent Decrease in the Oxygen Transfer Rate With Respect to Succinic Acid)

In Example 10, succinic acid was produced in the same manner as in Example 8 except that, since the liquid amount is increased in association with the addition of the above-described neutralizing agent and this causes changes in the oxygen transfer rate, the amount of reaction solution was maintained constant by removing the same amount of the reaction solution as that of the added neutralizing agent from the reaction vessel to eliminate the effects of changes in the oxygen transfer rate caused by changes in the liquid amount. The oxygen transfer rate (mmol-$O_2$/L/hr), oxygen transfer rate retention rate (%), succinic acid production rate (mmol-SA/L/hr), percent decrease in the oxygen transfer rate with respect to succinic acid (%/g/L), succinic acid concentration (g/L), ratio of the oxygen transfer rate to the succinic acid production rate (mmol-$O_2$/mol-SA) and doubling time, which were measured after 20 hours of incubation, are shown in Table 2.

It is noted here that the "oxygen transfer rate retention rate (%)" indicates a ratio of the oxygen transfer rate after 20 hours with respect to the oxygen transfer rate at time 0.

Example 11

Succinic acid was produced in the same manner as in Example 10 except that no aeration was performed. The reaction results are shown in Table 2.

TABLE 2

|  |  | Example 10 | Example 11 |
|---|---|---|---|
| Aeration |  | 100 mL/min | not performed |
| Oxygen transfer rate (mmol-$O_2$/L/hr) | at 0 hour | 0.91 | 0.91 |
|  | at 20 hours | 0.91 | 0.05 |
| Oxygen transfer rate retention rate (%) |  | 100% | 5.30% |
| Succinic acid production rate (mmol-SA/L/hr) |  | 30.8 | 29.8 |
| Percent decrease in the oxygen transfer rate with respect to succinic acid (%/g/L) |  | 0% | 1.33% |
| Succinic acid concentration (g/L) |  | 73.6 | 71.1 |
| Ratio of the oxygen transfer rate to the succinic acid production rate (mmol-$O_2$/mol-SA) |  | 29.6 | 16.1 |
| Doubling time (hr) |  | >40 | >40 |

It was found that it is more preferable to control the oxygen transfer rate by aeration, specifically, to control the oxygen transfer rate such that it does not decrease by 1.2% or more when 1 g of succinic acid is produced per 1 L of reaction solution.

From the above, it was revealed that, as a result of controlling the oxygen supply and the amount of succinic acid production in the reaction vessel, a higher yield of succinic acid and a higher succinic acid production rate can be attained as compared to those cases of anaerobic reaction and microaerobic reaction performed in Comparative Examples.

Industrial Applicability

According to the method of the present invention, as compared to conventional methods, the yield of succinic acid and the succinic acid production rate can be improved and the amount of by-products (such as pyruvic acid), which were conventionally generated under anaerobic conditions, can be reduced.

Further, according to the present invention, a succinic acid production method, which is applicable at an industrial scale without requiring enhancement of installations and reaction control for creating a completely anaerobic environment, can be provided. The resulting succinic acid can be used in food additives, pharmaceuticals, cosmetics, industrial materials and the like. Moreover, by performing polymerization reaction using the resulting succinic acid as a starting material, a succinic acid-containing polymer can also be produced.

The invention claimed is:

1. A method of producing succinic acid, comprising allowing a microorganism having a succinic acid-producing ability to react with a sugar, wherein the ratio of oxygen transfer rate to succinic acid production rate is 0.1 to 240 mmol-$O_2$/mmol-SA and doubling time of said microorganism during reaction is not shorter than 40 hours.

2. The method according to claim 1, wherein percent decrease in oxygen transfer rate with respect to succinic acid (%/g/L) in said reaction is not higher than 1.2.

3. The method according to claim 1, wherein said oxygen transfer rate (mmol-$O_2$/L/hr) in said reaction is 0.01 to 5.

4. The method according to claim 1, wherein said microorganism is selected from the group consisting of coryneform bacteria, *Escherichia coli*, bacteria belonging to the genus *Anaerobiospirillum*, bacteria belonging to the genus *Actinobacillus*, filamentous fungi and yeasts.

5. The method according to claim 1, wherein said microorganism has been modified so that lactate dehydrogenase activity is reduced as compared to an unmodified strain and/or pyruvate carboxylase activity is enhanced as compared to an unmodified strain.

6. The method according to claim 1, wherein pH during said reaction is 5 to 10.

7. The method according to claim 1, wherein the ratio of the oxygen transfer rate to the succinic acid production rate is from 0.38 to 105.82 mmol-$O_2$/mmol-SA.

8. The method according to claim 1, wherein the ratio of the oxygen transfer rate to the succinic acid production rate is from 0.38 to 9.88 mmol-$O_2$/mmol-SA.

9. The method according to claim 1, wherein the carbon yield of succinic acid against consumed sugar is from 80.2 to 81.9 C-mol%, and the ratio of the oxygen transfer rate to the succinic acid production rate is from 1.17 to 59.03 mmol-$O_2$/mmol-SA.

10. The method according to claim 1, wherein the percent decrease in the oxygen transfer rate with respect to succinic acid is from 0.63 to 1.0%/g/L.

11. The method according to claim 1, wherein the acetic acid-to-succinic acid weight ratio is from 10.3 to 15.3%.

12. The method according to claim 1, wherein the microorganism is allowed to react with the sugar in a reaction solution, and the amount of the reaction solution is maintained constant.

13. The method according to claim 12, further comprising adding a neutralizing agent to the reaction solution while removing a portion of the reaction solution so that the amount of the reaction solution is maintained constant.

14. The method according to claim 1, wherein the oxygen transfer rate is from 0.01 to 2.61 mmol-$O_2$/L/hr.

15. The method according to claim 1, wherein the oxygen transfer rate is from 0.05 to 1.46 mmol-$O_2$/L/hr.

16. A method of producing a succinic acid-containing polymer, comprising producing succinic acid by the method according to claim 1; and performing polymerization reaction using the resulting succinic acid.

17. A method of producing a succinic acid derivative, comprising producing succinic acid by the method according to claim 1; and synthesizing a succinic acid derivative using the resulting succinic acid as a starting material.

* * * * *